US00PP27644P3

(12) United States Plant Patent
Hamilton et al.

(10) Patent No.: US PP27,644 P3
(45) Date of Patent: Feb. 7, 2017

(54) RASPBERRY PLANT NAMED 'DRISRASPEIGHT'

(50) Latin Name: ***Rubus idaeus* L.**
Varietal Denomination: DrisRaspEight

(71) Applicant: DRISCOLL STRAWBERRY ASSOCIATES, INC., Watsonville, CA (US)

(72) Inventors: Brian K. Hamilton, Richmond, TX (US); Marta C. Baptista, Camarillo, CA (US); Matthias D. Vitten, Aptos, CA (US)

(73) Assignee: Driscoll's, Inc., Watsonville, CA (US)

( * ) Notice: Subject to any disclaimer, the term of this patent is extended or adjusted under 35 U.S.C. 154(b) by 18 days.

(21) Appl. No.: 14/544,622

(22) Filed: Jan. 28, 2015

(65) Prior Publication Data

US 2016/0219774 P1 Jul. 28, 2016

(51) Int. Cl.
*A01H 5/08* (2006.01)

(52) U.S. Cl.
USPC ..... Plt./204

(58) Field of Classification Search
USPC ..... Plt./156, 226, 204
See application file for complete search history.

(56) References Cited

U.S. PATENT DOCUMENTS

| | | | |
|---|---|---|---|
| PP11,067 | P | 9/1999 | Fear et al. |
| PP11,087 | P | 10/1999 | Fear et al. |
| PP11,094 | P | 10/1999 | Fear et al. |
| PP11,102 | P | 10/1999 | Fear et al. |
| PP14,761 | P2 | 5/2004 | Fear et al. |
| PP14,781 | P2 | 5/2004 | Fear et al. |
| PP14,804 | P2 | 5/2004 | Fear et al. |
| PP14,860 | P2 | 6/2004 | Fear et al. |
| PP14,903 | P2 | 6/2004 | Fear et al. |
| PP14,904 | P2 | 6/2004 | Fear et al. |
| PP18,658 | P3 | 3/2008 | Fear et al. |
| PP18,659 | P3 | 3/2008 | Fear et al. |
| PP19,137 | P3 | 8/2008 | Harrison et al. |
| PP19,656 | P2 | 1/2009 | Hamilton et al. |
| PP22,246 | P3 | 11/2011 | Hamilton et al. |
| PP22,731 | P2 | 5/2012 | Fear et al. |
| PP23,477 | P3 | 3/2013 | Hamilton et al. |
| PP24,610 | P3 | 7/2014 | Hamilton et al. |
| PP25,044 | P3 | 11/2014 | Hamilton et al. |
| PP25,045 | P3 | 11/2014 | Hamilton et al. |

*Primary Examiner* — Susan McCormick Ewoldt
*Assistant Examiner* — Karen Redden
(74) *Attorney, Agent, or Firm* — Morrison & Foerster LLP

(57) ABSTRACT

A new and distinct variety of raspberry plant named 'DrisRaspEight' particularly distinguished by having a self-fruitful plant that bears medium-sized, glossy berries, is disclosed.

2 Drawing Sheets

Genus and species: *Rubus idaeus* L.
Variety denomination: 'DrisRaspEight'.

BACKGROUND OF THE NEW PLANT

The present invention relates to a new and distinct raspberry variety designated 'DrisRaspEight' and botanically known as *Rubus idaeus* L. This new raspberry variety was discovered in Ventura County, Calif. in October 2008 and originated from a cross between the proprietary female parent raspberry plant 'Driscoll Estrella' (U.S. Plant Pat. No. 19,137) and the proprietary male parent raspberry plant 'DrisRaspFour' (U.S. Plant Pat. No. 22,731). The original seedling of the new variety was first asexually propagated via tissue culture at a nursery in Santa Cruz County, Calif. in 2008. 'DrisRaspEight' was subsequently asexually propagated and underwent further testing at a nursery in Santa Cruz County, Calif. for seven years. The present invention has been found to be stable and reproduce true to type through successive asexual propagations via tissue culture and root cuttings.

SUMMARY OF THE INVENTION

The following are the most outstanding and distinguishing characteristics of this new variety when grown under normal horticultural practices in Santa Cruz County, Calif.:

1. Self-fruitful plant; and
2. Medium-sized, glossy berries.

DESCRIPTION OF THE PHOTOGRAPHS

This new raspberry plant is illustrated by the accompanying photographs which show cane, leaves, flowers and fruit of the new plant. The colors shown are as true as can be reasonably obtained by conventional photographic procedures. The photographs are of plants that are eleven months old.

DESCRIPTION OF THE NEW VARIETY

Figure 1:
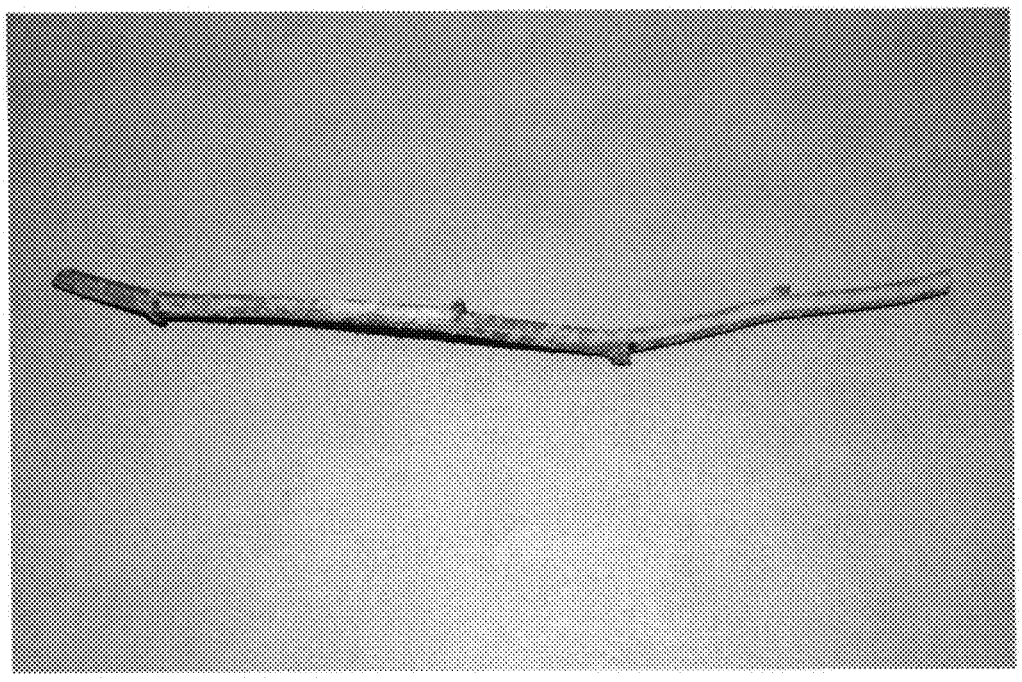
FIG. 1 shows a section of a young cane with prickles.
Figure 2:
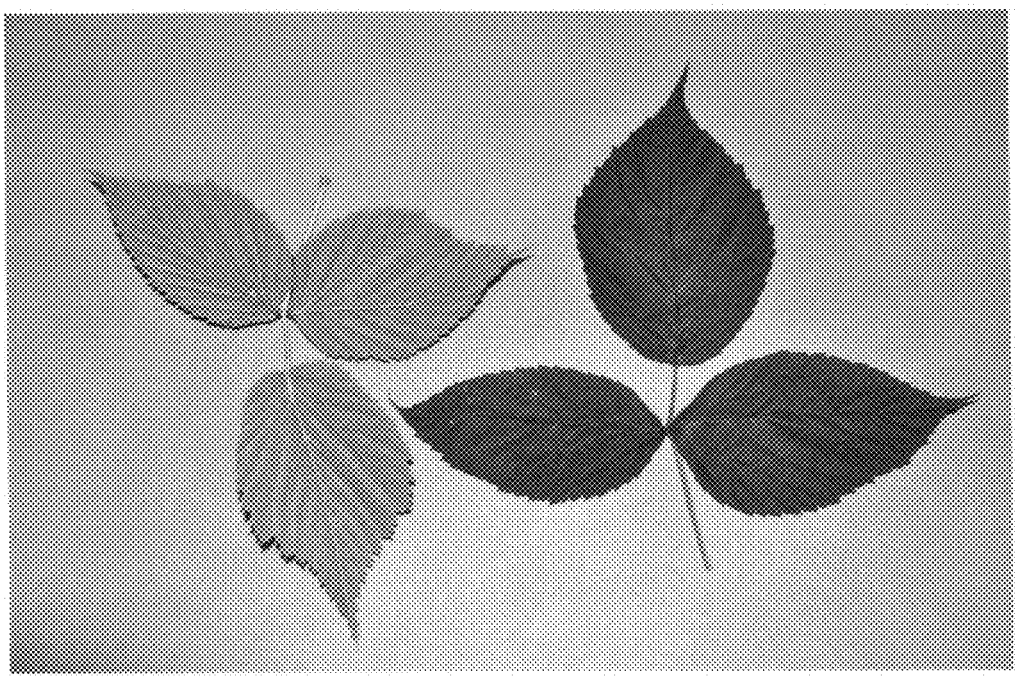
FIG. 2 shows both the upper surface and the lower surface of the plant leaves.
Figure 3:
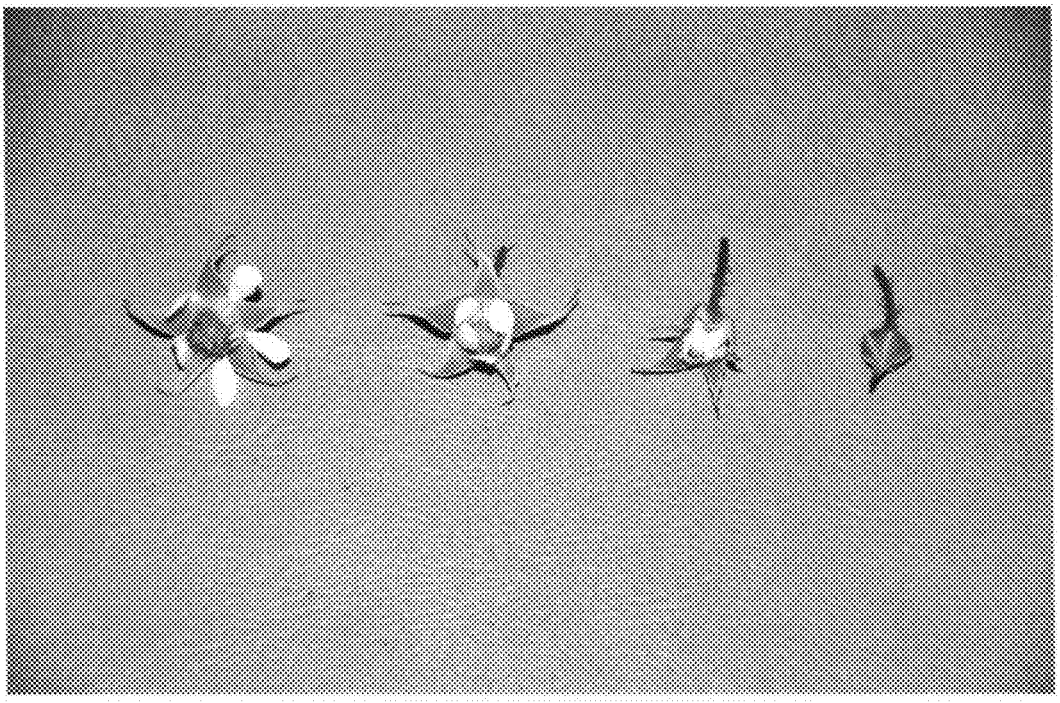
FIG. 3 shows close-up views of typical flowers at various stages of development.
Figure 4:
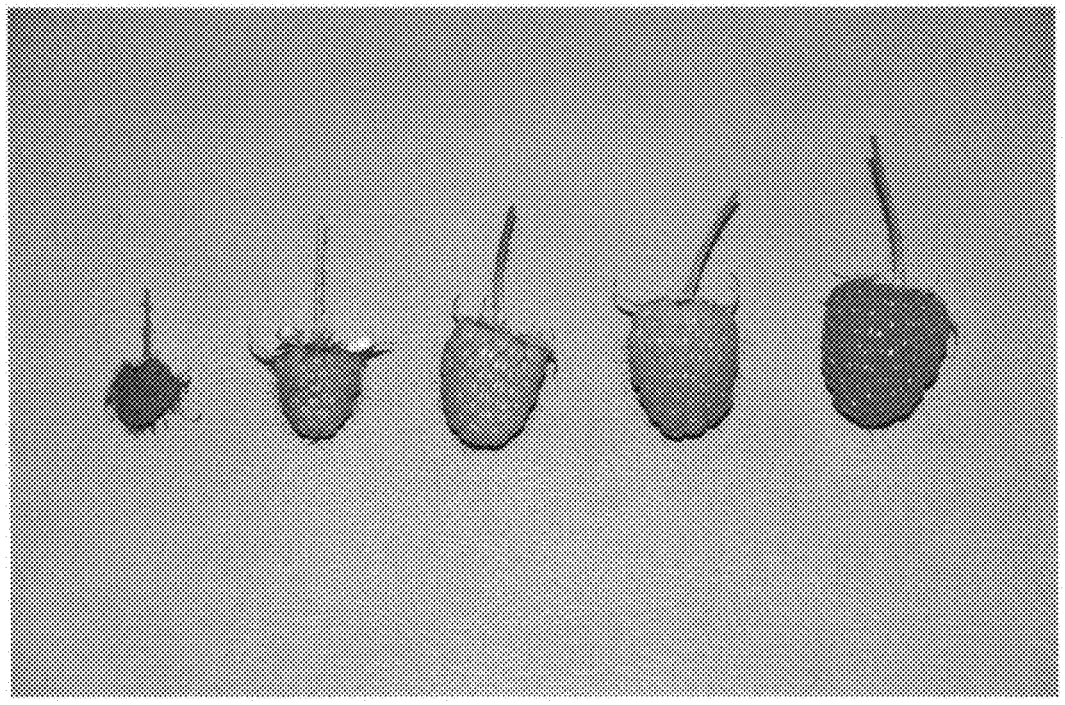
FIG. 4 shows close-up views of typical fruit at various stages of development.

The following detailed descriptions set forth the distinctive characteristics of 'DrisRaspEight'. The data which define these characteristics is based on observations taken in Santa Cruz County, Calif. from 2008 to 2014. This description is in accordance with UPOV terminology. Color designations, color descriptions, and other phenotypical descriptions may deviate from the stated values and descriptions depending upon variation in environmental, seasonal, climatic and cultural conditions. 'DrisRaspEight' has not been observed under all possible environmental conditions. The botanical description of 'DrisRaspEight' was taken from eleven-month-old plants. Color references are primarily to The R.H.S. Colour Chart of The Royal Horticultural Society of London (R.H.S.) (2007 edition). Descriptive terminology follows the *Plant Identification Terminology, An Illustrated Glossary,* 2$^{nd}$ edition by James G. Harris and Melinda Woolf Harris, unless where otherwise defined.

DETAILED BOTANICAL DESCRIPTION

Classification:
- *Family*.—Rosaceae.
- *Botanical*.—*Rubus idaeus* L.
- *Common name*.—Raspberry.
- *Variety name*.—'DrisRaspEight'.

Parentage:
- *Female parent*.—The proprietary raspberry plant 'Driscoll Estrella' (U.S. Plant Pat. No. 19,137).
- *Male parent*.—The proprietary raspberry plant 'DrisRaspFour' (U.S. Plant Pat. No. 22,731).

Plant:
- *Propagation*.—Tissue culture and root cuttings.
- *Size*.—Large.
- *Height*.—193.0 cm.
- *Width*.—176.8 cm.
- *Length/width ratio*.—1.1.
- *Productivity*.—Productivity of plants that were six-months old or older ranged from 3.51 kg/meter to 8.28 kg/meter of fruit per season when grown in Watsonville, Calif.
- *Self-fruitfulness*.—Self-fruitful.
- *New cane growth habit*.—Semi-erect.

Primocanes:
- *Number of canes*.—Medium; 146.
- *Glaucosity (waxy bloom) on full grown shoot after picking*.—Medium.
- *Cane length in autumn*.—Medium.
- *Cane length for current season's cane in autumn*.—146.0 cm.
- *Length of internode*.—Medium.
- *Internodal distance at central ⅓ of cane*.—6.65 cm.
- *Anthocyanin coloration of apex during rapid growth*.—Absent.
- *Intensity of anthocyanin coloration of apex during rapid growth*.—Absent.
- *Time of cane emergence*.—Early.
- *Time of beginning of flowers*.—Early June to mid-September.
- *Time of beginning of fruit ripening*.—Early.
- *Length of fruiting period*.—Late March to late June.
- *Percent of cane flowering as primocane*.—40%.
- *Percent primocane yield of total yield*.—50%.
- *Glaucosity (waxy bloom) on current years cane in autumn*.—Strong.
- *Cane strength*.—Strong.
- *Shape of cane cross section*.—Rounded.
- *Pubescence on canes*.—Absent.

Floricanes:
- *Dormant cane length in summer*.—Medium (Pruned).
- *Dormant cane color in summer*.—RHS 168C (Medium greyed-orange).
- *Fruiting lateral attitude*.—Semi-erect.
- *Fruiting lateral length*.—Medium; 23.61 cm.
- *Time of beginning of flowers*.—Late March to late June.
- *Time of beginning of fruit ripening*.—Mid-July to late July.
- *Length of fruiting period*.—Mid-July to late July.

Prickles (spines):
- *Density of spines on central third*.—Medium.
- *Size of base of prickles*.—Small.
- *Length (from base to tip)*.—Short.
- *Length at* 1.0 *m height at end of harvest season (from base to tip)*.—1.42 mm.
- *Color (pigmentation)*.—RHS 183C (Dark greyed-purple).
- *Attitude of tip*.—Horizontal.
- *Size*.—Small.
- *Presence and distribution on petioles*.—Present and regularly distributed.

Leaves:
- *Terminal leaflet*.—Length: Medium; 11.97 cm. Width: Medium; 8.95 cm. Length/width ratio: 1.3. Leaf color: Upper surface: RHS 137A (Dark green). Lower surface: RHS 191A (Medium greyed-green). Profile in cross section: Concave. Relief between the veins: Strong. Overlapping of leaflets: Free. Glossiness: Dull. Shape: Ovate. Apex: Acuminate. Base: Obtuse. Margin: Crenate. Arrangement: Simple.
- *Lateral leaflets (basal pair)*.—Number of leaflets: Always 3. Size: Length: 10.28 cm. Width: 6.67 cm. Length/width ratio: 1.5. Arrangement: Compound-opposite (2 leaves per node). Shape: Ovate. Apex: Acuminate. Base: Obtuse. Margin: Doubly serrate. Lateral leaflet (length to stalklet, lower pair): Medium.
- *Rachis length between terminal leaflet and adjacent lateral leaflets*.—30.8 mm.
- *Petiole*.—Size: Length: 4.0 mm. Diameter: 1.97 mm. Pigmentation: Upper surface: RHS 143C (Medium green). Lower surface: RHS 143C (Medium green).

Stipules:
- *Orientation*.—Erect.

Flowers:
- *Size*.—Medium.
- *Diameter*.—21.84 mm.
- *Color*.—RHS 157B (Light green-white).
- *Petal length*.—8.8 mm.
- *Petal width*.—4.23 mm.
- *Length/width ratio*.—2.1.
- *Flowering period*.—Primocane: Early June to mid-September. Floricane: Late March to late June.
- *Pedicel*.—Number of spines: Few. Anthocyanin coloration: Absent. Length: Medium; 30.92 mm. Diameter: 1.10 mm.

Peduncle:
- *Presence of anthocyanin coloration*.—Absent.
- *Intensity of anthocyanin coloration*.—Absent or very weak.

Fruit:
- *Length*.—Medium; 23.61 mm.
- *Width*.—Medium; 20.38 mm.
- *Ratio of length to width*.—1.2, as long as broad.

*Average number of drupelets per fruit.*—75.
*Weight (g/fruit).*—Primocane: 4.9. Floricane: 6.0.
*Soluble solids (% in Brix).*—10.8.
*Weight of seeds (g/seed).*—0.002347.
*Size.*—Medium.
*Shape.*—Ovate (Broad conical).
*Size of single drupelet.*—75 mm.
*Color.*—Immature fruit: RHS 138C (Light green). Maturing fruit: RHS 32A (Dark orange-red). Mature fruit color: RHS 185A (Dark greyed-purple).
*Glossiness.*—Strong.
*Firmness.*—Medium.
*Adherence to plug.*—Easy.
*Main bearing type.*—Both on previous year's cane in summer and on current year's cane in autumn.
*Time of ripening.*—Primocane: Medium. Floricane: Medium.
*Harvest season.*—Primocane: Mid-July to late July. Floricane: Mid-July to late July.
*Yield.*—Yield from plants that were six-months old or older ranged from 3.51 kg/meter to 8.28 kg/meter per season when grown in Watsonville, Calif.

Pest and disease resistance: Not tested.

COMPARISON WITH PARENTAL AND COMMERCIAL VARIETIES

'DrisRaspEight' differs from the proprietary female parent 'Driscoll Estrella' (U.S. Plant Pat. No. 19,137) in that 'DrisRaspEight' is more vigorous and has larger fruit of better quality than 'Driscoll Estrella'.

'DrisRaspEight' differs from the proprietary male parent 'DrisRaspFour' (U.S. Plant Pat. No. 22,731) in that 'DrisRaspEight' has better quality and brighter colored fruit with a higher yield than 'DrisRaspFour'.

'DrisRaspEight' differs from commercial variety 'Driscoll Maravilla' (U.S. Plant Pat. No. 14,804) in that 'DrisRaspEight' has strongly glossy, medium firm fruit having an easy adherence to the plug, whereas 'Driscoll Maravilla' has medium glossy, firm fruit having a medium adherence to the plug.

We claim:

1. A new and distinct variety of raspberry plant named 'DrisRaspEight', substantially as illustrated and described herein.

* * * * *